(12) United States Patent
Goetz

(10) Patent No.: US 12,324,741 B2
(45) Date of Patent: Jun. 10, 2025

(54) MEDICAL CHAMBER SYSTEM, INTRODUCTION SYSTEM AND KIT

(71) Applicant: ARTRACT MEDICAL INC., New York, NY (US)

(72) Inventor: Wolfgang Goetz, Regensburg (DE)

(73) Assignee: ARTRACT MEDICAL INC., New York, NY (US)

( * ) Notice: Subject to any disclaimer, the term of this patent is extended or adjusted under 35 U.S.C. 154(b) by 949 days.

(21) Appl. No.: 17/309,694

(22) PCT Filed: Jan. 23, 2020

(86) PCT No.: PCT/EP2020/051633
§ 371 (c)(1),
(2) Date: Jun. 15, 2021

(87) PCT Pub. No.: WO2020/152273
PCT Pub. Date: Jul. 30, 2020

(65) Prior Publication Data
US 2022/0031458 A1    Feb. 3, 2022

(30) Foreign Application Priority Data
Jan. 24, 2019    (DE) .................... 10 2019 101 771.8

(51) Int. Cl.
*A61F 2/24* (2006.01)
*A61M 60/187* (2021.01)
(Continued)

(52) U.S. Cl.
CPC .......... *A61F 2/2487* (2013.01); *A61F 2/2481* (2013.01); *A61M 60/187* (2021.01);
(Continued)

(58) Field of Classification Search
CPC .................. A61F 2/2487; A61F 2/2481; A61F 2002/2484; A61F 2220/0008;
(Continued)

(56) References Cited

U.S. PATENT DOCUMENTS 2,826,193 A    3/1958    Vineberg
3,034,501 A    5/1962    Hewson
(Continued)

FOREIGN PATENT DOCUMENTS

CN    107810017 A    3/2018
EP    1176998 B1    9/2008
(Continued)

OTHER PUBLICATIONS

International Search Report and Written Opinion for PCT/EP2020/051633 mailed Apr. 23, 2020.

*Primary Examiner* — Eugene T Wu
(74) *Attorney, Agent, or Firm* — Aird & McBurney LP

(57) ABSTRACT

The present invention relates to a medical chamber system (700) for implantation in the chest of a patient to support the heart activity, preferably by displacing the heart apex (105), comprising at least a first chamber (702) for arrangement inside the heart sac (300) and a second chamber (701) for arrangement outside the heart sac (300), wherein the chambers (701, 702) comprise at least one connection portion or connection channel (703) which connects the two chambers (701, 702) to each other, the chambers (701, 702) and the connection channel (703) are further embodied to be filled with fluid (705) and, preferably in the implanted state, to be arranged such that the heart activity acts on the first chamber (702) and that the second chamber (701) acts as a volume storage and/or energy storage for the fluid (705). Furthermore, the present invention relates to an introduction system for a medical chamber system (700) and to a kit, encom- (Continued)

passing a medical chamber system (700) and an introduction system.

11 Claims, 12 Drawing Sheets

(51) Int. Cl.
*A61M 60/191* (2021.01)
*A61M 60/289* (2021.01)
*A61M 60/531* (2021.01)
*A61M 60/867* (2021.01)
*A61M 60/869* (2021.01)

(52) U.S. Cl.
CPC ........ *A61M 60/191* (2021.01); *A61M 60/289* (2021.01); *A61M 60/531* (2021.01); *A61M 60/867* (2021.01); *A61M 60/869* (2021.01); *A61F 2002/2484* (2013.01); *A61F 2220/0008* (2013.01); *A61F 2250/0003* (2013.01)

(58) Field of Classification Search
CPC ......... A61F 2250/0003; A61M 60/187; A61M 60/191; A61M 60/289; A61M 60/531; A61M 60/867; A61M 60/869; A61M 60/468
See application file for complete search history.

(56) References Cited

U.S. PATENT DOCUMENTS

| | | | |
|---|---|---|---|
| 4,957,477 A * | 9/1990 | Lundback | A61M 60/191 600/16 |
| 5,119,804 A | 6/1992 | Anstadt | |
| 5,386,528 A | 1/1995 | Ando et al. | |
| 6,224,540 B1 | 5/2001 | Lederman et al. | |
| 6,602,182 B1 | 8/2003 | Milbocker | |
| 6,663,558 B2 | 12/2003 | Lau et al. | |
| 6,808,483 B1 | 10/2004 | Ortiz et al. | |
| 7,641,686 B2 | 1/2010 | Lashinski et al. | |
| 7,871,366 B2 | 1/2011 | Criscione et al. | |
| 7,935,045 B2 | 5/2011 | Criscione et al. | |
| 8,075,471 B2 | 12/2011 | Trumble | |
| 8,944,986 B2 | 2/2015 | Altman et al. | |
| 9,259,520 B2 | 2/2016 | Altman et al. | |
| 9,510,746 B2 | 12/2016 | Criscione et al. | |
| 9,572,661 B2 | 2/2017 | Robin et al. | |
| 9,642,957 B2 | 5/2017 | Criscione et al. | |
| 9,833,318 B2 | 12/2017 | Criscione et al. | |
| 9,833,551 B2 | 12/2017 | Criscione et al. | |
| 2002/0065449 A1 | 5/2002 | Wardle | |
| 2002/0188170 A1 | 12/2002 | Santamore et al. | |
| 2003/0233022 A1 | 12/2003 | Vidlund et al. | |
| 2004/0249236 A1 * | 12/2004 | Hegde | A61M 60/515 600/16 |
| 2005/0171589 A1 * | 8/2005 | Lau | A61F 2/2481 607/129 |
| 2006/0178550 A1 | 8/2006 | Jenson | |
| 2008/0183286 A1 | 7/2008 | Vaska | |
| 2009/0036730 A1 | 2/2009 | Criscione et al. | |
| 2011/0021864 A1 | 1/2011 | Criscione et al. | |
| 2012/0142996 A1 | 6/2012 | Criscione | |
| 2012/0277855 A1 | 11/2012 | Lashinski et al. | |
| 2013/0041458 A1 | 2/2013 | Lashinski et al. | |
| 2013/0102849 A1 * | 4/2013 | Criscione | A61M 60/289 600/204 |
| 2014/0194669 A1 | 7/2014 | Wildhirt et al. | |
| 2015/0148590 A1 | 5/2015 | de Canniere | |
| 2015/0165104 A1 | 6/2015 | Criscione et al. | |
| 2017/0080137 A1 | 3/2017 | Criscione et al. | |
| 2017/0368246 A1 | 12/2017 | Criscione et al. | |
| 2018/0193147 A1 | 7/2018 | Criscione et al. | |

FOREIGN PATENT DOCUMENTS

| | | |
|---|---|---|
| EP | 2752208 A1 | 7/2014 |
| EP | 2482865 B1 | 5/2015 |
| EP | 2987513 B1 | 7/2022 |
| JP | 2010529866 A | 9/2010 |
| WO | 2004066805 A3 | 8/2004 |

* cited by examiner

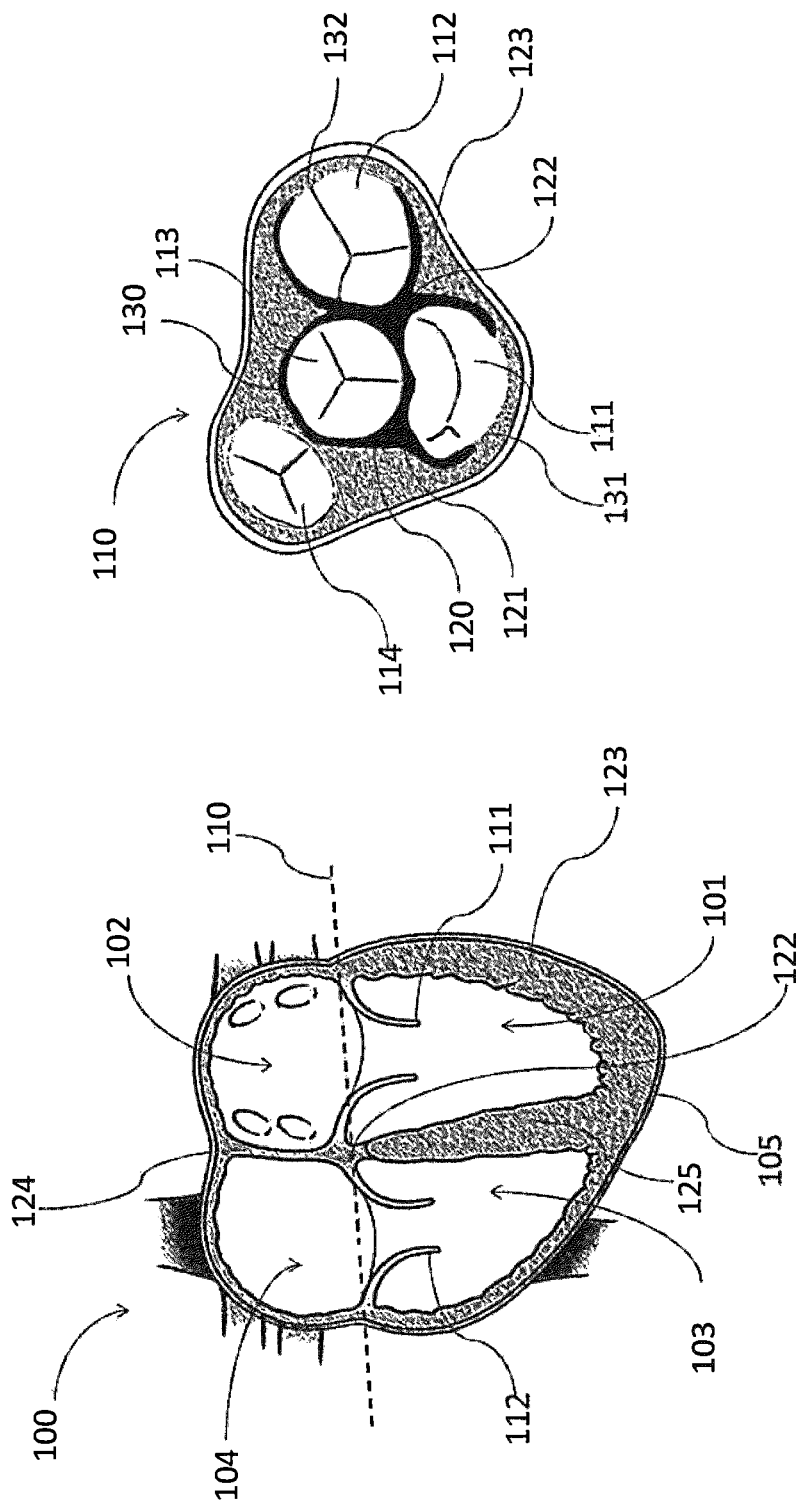

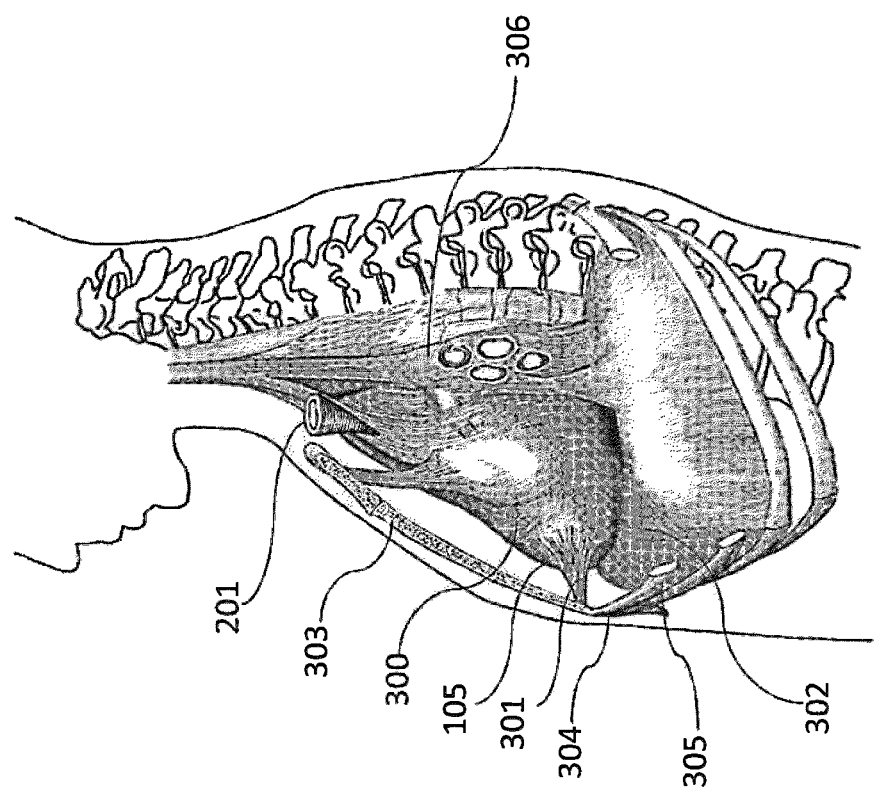

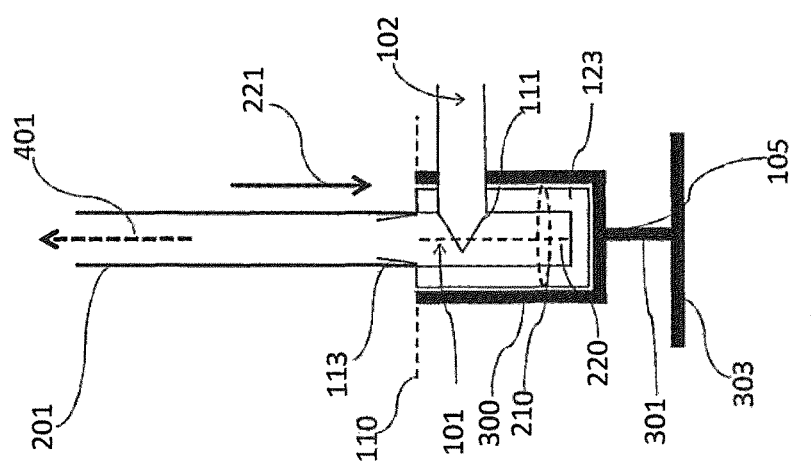
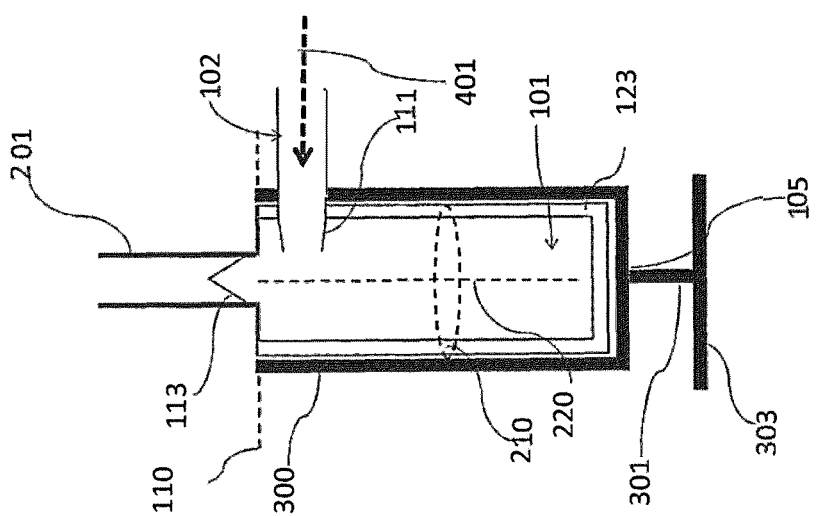

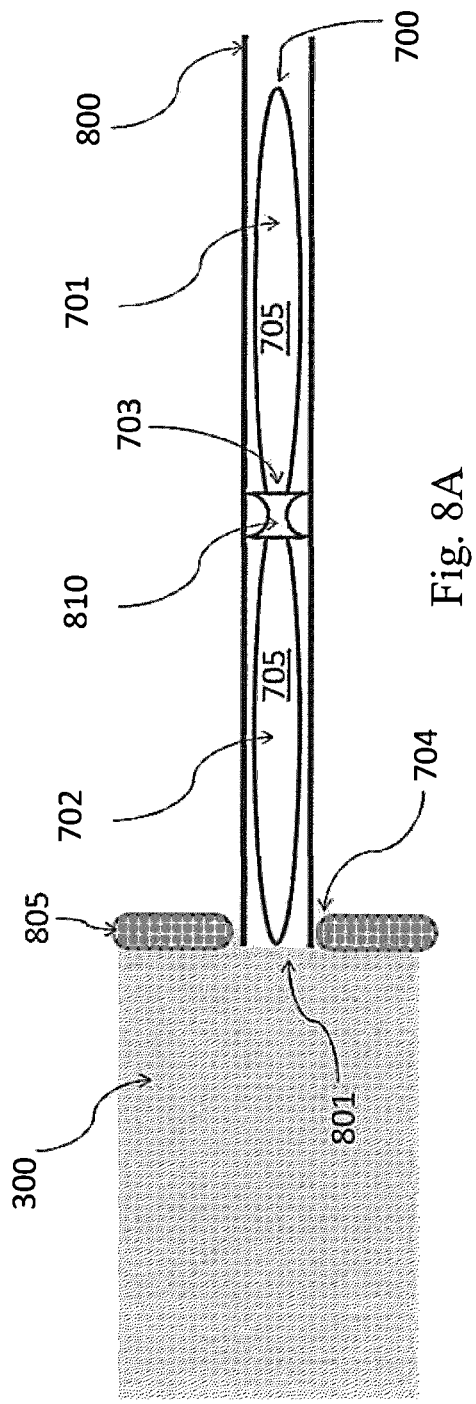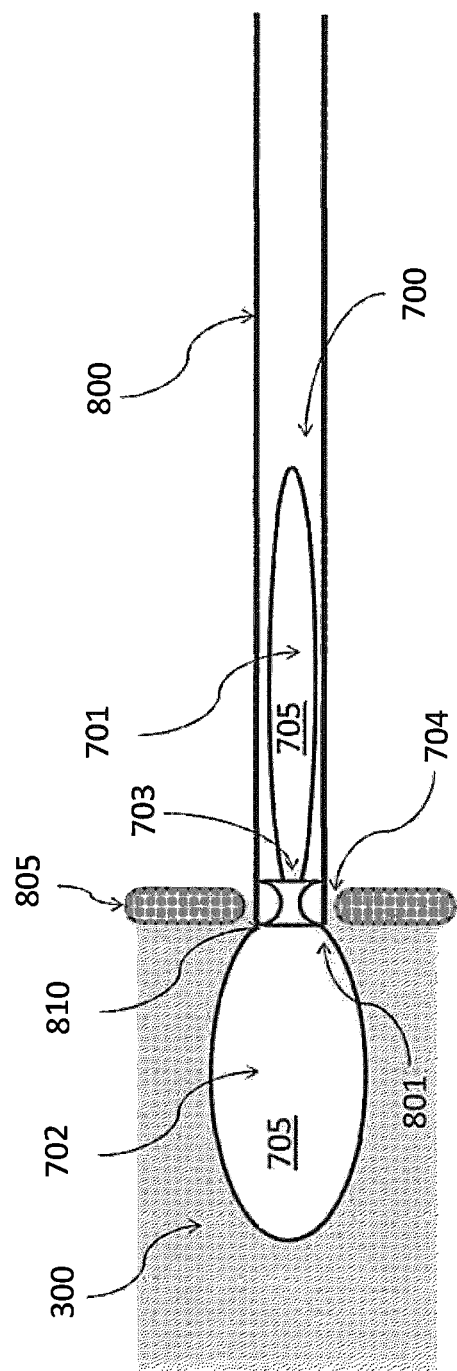

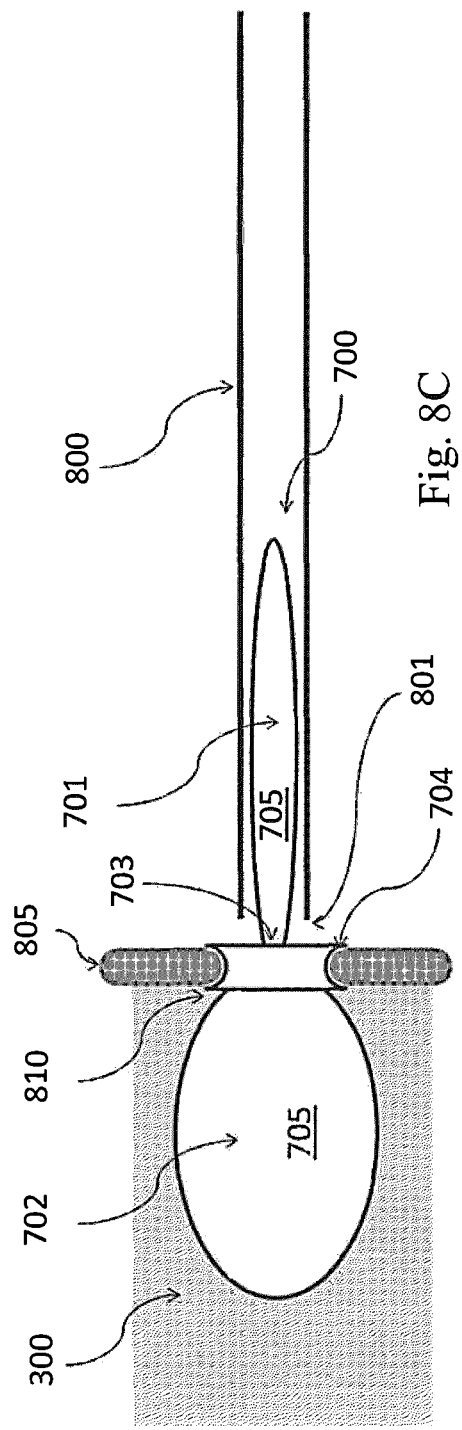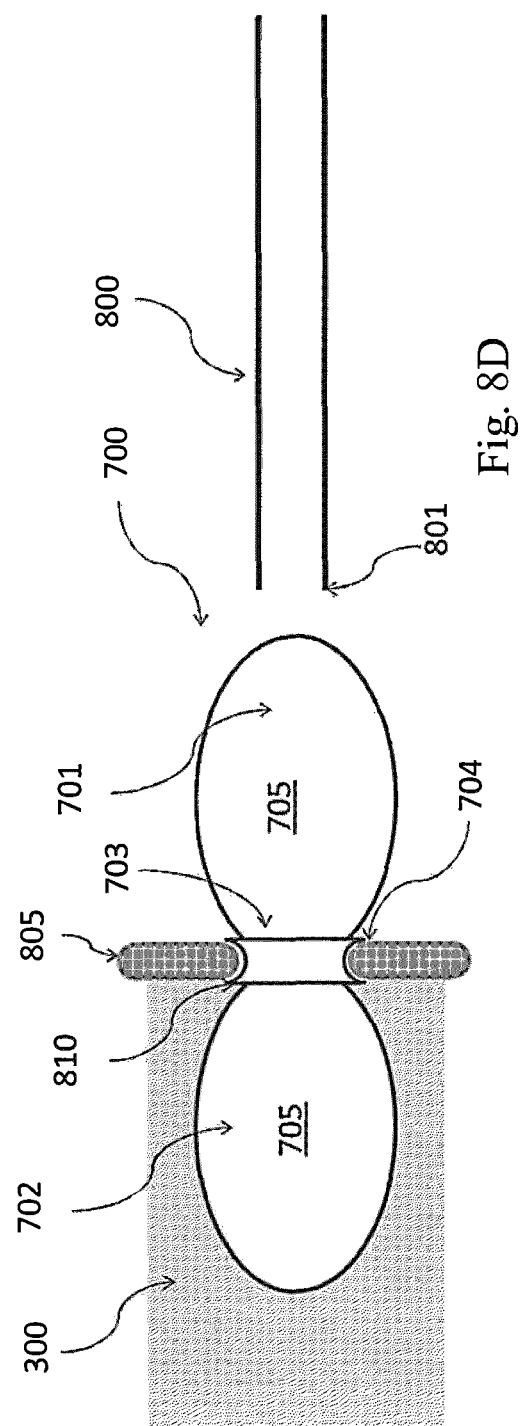

MEDICAL CHAMBER SYSTEM, INTRODUCTION SYSTEM AND KIT

The present invention relates to a medical chamber system, an introduction system and a kit.

Known for the care of patients with heart failure are various systems for heart support or support of the heart activity, as for example from US 2017/0368246 A1, EP 2 482 865 B1 or US 2018/0193147 A1. For example, there are left ventricular and/or right ventricular heart support systems that may be actively driven. The systems may be fully implanted.

It is the object of the present invention to provide a further system, an introduction system for the system and a kit encompassing the system and the introduction system.

The object according to the present invention may be achieved by the medical chamber system of claim 1, by the introduction system of claim 9 and by the kit of claim 10.

The object according to the present invention may be achieved by providing a medical chamber system (hereinafter also in short: chamber system) for implantation in the chest of a patient to support the heart activity, with which preferably the patient's heart apex may be displaced or shifted.

The medical chamber system encompasses at least a first chamber, provided to be arranged inside a heart sac of the patient, and a second chamber, provided to be arranged outside of the heart sac. These two chambers comprise at least one connecting section or one connection channel which connects the lumen or the interior of the two chambers to each other. The chambers are designed to be filled with a fluid.

The two chambers are preferably provided and designed to be arranged, in the implanted state of the chamber system, such that the heart activity displaces fluid from the first chamber by applying pressure and thereby transfers it into the second chamber. The second chamber thereby preferably acts as a volume storage and/or energy storage for the fluid or parts thereof within the chamber system.

The chambers may be provided such that they allow, when acted upon by pressure on their chamber walls, a volume displacement, not actively supported or caused by a component, between one of the two chambers and the other of these chambers and/or, after implantation of the chamber system, between a space in the heart sac and a space outside the heart sac. In this way, the displacement of the heart apex and thus an axial shortening of the heart chambers may be achieved or supported.

The chamber system according to the present invention is preferably designed to enable a volume shift between a space inside the heart sac and a space outside the heart sac, which is driven by the change in volume of the heart chambers.

The present invention further relates to an introduction system for the chamber system. The introduction system serves for implanting the chamber system according to the present invention into the patient. The introduction system may comprise one or several of the following components: insertion catheter, guiding catheter, guiding wire, dilatator and delivery or supply catheter, chamber system according to the present invention. The cross-section of the insertion catheter and/or lumen may be round, oval or polygonal. In this, in several embodiments, the introduction system may also comprise several exemplars of the respective catheters and/or of said guiding wire.

The present invention also relates to a kit which comprises a chamber system according to the present invention and an introduction system according to the present invention.

In the context of the present invention, a patient can be a human or an animal.

In all of the following statements, the use of the expression "may be" or "may have" and so on, is to be understood synonymously with "preferably is" or "preferably has," and so on respectively, and is intended to illustrate embodiments according to the present invention.

Whenever numerical words are mentioned herein, the person skilled in the art shall recognize or understand them as indications of numerical lower limits. Unless it leads the person skilled in the art to an evident contradiction, the person skilled in the art shall comprehend for example the specification of "one" as encompassing "at least one". This understanding is also equally encompassed by the present invention as the interpretation that a numerical word, for example, "one" may alternatively mean "exactly one", wherever this is evidently technically possible for the person skilled in the art. Both understandings are encompassed by the present invention and apply to all numerical words used herein.

Unless otherwise stated below, proximal means towards the center of the body and distal means away from the center of the body.

Advantageous developments of the present invention are each subject-matter of the dependent claims and of embodiments.

Whenever an embodiment is mentioned herein, it is then to be understood as an exemplary embodiment according to the present invention which is not to be understood as limiting.

Embodiments according to the present invention may comprise one or more of the features mentioned above and/or below in any combination, unless the skilled person recognizes such a combination as being technically impossible.

Previously described systems for active support of the heart function, see e.g. the above-mentioned US 2017/0368246 A1, EP 2 482 865 B1 or US 2018/0193147 A1, support heart activity and compress the heart chambers by an active component, such as a mechanical component. This component may be, or may comprise, a motor that, directly or indirectly, acts on the heart muscle hydraulically, electrically, magnetically, electromagnetically, mechanically, or the like and/or contacts the latter.

In contrast thereto, the chamber system according to the present invention preferably does not operate an active mechanical support of the heart activity with an active mechanical component and/or does not compress the heart chambers and/or has, in particular for this purpose, no device, in particular no motor, which directly or indirectly acts hydraulically, electrically, magnetically, electromagnetically, mechanically or the like on the heart muscle and/or has a pumping effect, and/or no control or control device set up to act on a motor, and/or is not connected to such a motor nor to such a control or control device in signal transmission.

The chamber system according to the present invention may preferably restore or contribute to the physiological shortening of the long axis of the heart chambers in the heart cycle, in that the natural heart activity moves the fluid contained in the chamber system from the first chamber into the second chamber and back again, thus allowing or supporting the shift of the heart apex toward the heart base and back again.

The first chamber and the second chamber (herein together also in short: chambers) may optionally be and/or be denoted as pressure chambers, pressure equalization or balance or compensation chambers, or the like.

The chambers may have a volume, a diameter, and/or a long axis and a short axis. The chambers may be designed similarly to each other or differently from each other.

The chambers may assume different shapes in use and optionally adapt to the surrounding anatomical structures and/or to the changing pressure conditions. In this, the chambers may be intentionally changed from a larger or more filled state to a smaller or less filled state and back to a larger state, in particular with regard to their size, shape and/or volume. This preferably occurs periodically, particularly preferably synchronously with the heart activity and/or effected by it.

The chamber system comprises at least one chamber wall, optionally one or exactly one separate chamber wall for each of the chambers. Thus, a chamber wall of the first chamber may be present or manufactured in one-piece together with a chamber wall of the second chamber, or the chamber wall of the first chamber may be connected to the chamber wall of the second chamber, e.g. via or with the inclusion of a support device further explained below.

In several embodiments according to the invention, at least one chamber wall is completely or at least partially flexibly deformable.

The chambers are designed in such that in the implanted state of the chamber system, the first chamber is located in the heart sac and the second chamber may be located outside the heart sac. The first chamber within the heart sac is preferably connected to the second chamber outside the heart sac via channels, preferably via a connection channel, such that fluid may flow from the first chamber in the heart sac into the second chamber outside the heart sac and back again. Valves or other means for regulating or controlling the flow between the chambers are not required and, in several embodiments, are not provided. In other embodiments, however, valves or other adjustable means for affecting the flow between the chambers are provided.

The shifting of the volume from one chamber to the other is driven by the heart activity in the heart sac. When the heart is filled, the increase of the heart volume in the heart sac shifts the fluid preferably from the first chamber present in the heart sac into the second chamber outside the heart sac. When the heart contracts, the decrease or reduction in the volume of the heart in the heart sac preferably shifts the fluid from the second chamber outside the heart sac to the first chamber within the heart sac. Due to the change in volume of the first chamber in the heart sac, the heart apex may move synchronously to the heart activity when the volume of the first chamber in the heart sac increases, and move away from the heart base when the first chamber within the heart sac decreases. By shifting the heart apex, the long axis of the heart chambers is shortened during the systole and lengthened during the diastole.

In several embodiments, the chamber system comprises more than two chambers. For example, the first chamber may be located in the heart sac, and one or more additional chambers may be located in the right chest cavity and/or in the left chest cavity and/or in the abdominal cavity. A further chamber may be located in other body structures, such as under the skin. A further chamber may be located outside the body. A further chamber may be the atmosphere. In this, connection channels of different lengths may exist between the chambers arranged in the heart sac and those chambers arranged outside the heart sac.

Preferably, in use, the chambers are implanted such that during the systole of the heart, fluid flows from the second chamber outside the heart sac into the first chamber in the heart sac and during the diastole, fluid flows from the first chamber in the heart sac into the second or further chamber(s) outside the heart sac. The change in the volume or the size of the first chamber in the heart sac enables the heart apex to be shifted, preferably in the axial direction, and thus to shorten the long axis of the heart chambers.

In several embodiments, the chamber system according to the present invention may be implanted completely surgically via an opening of the chest and/or of the abdominal cavity and/or via an open-heart operation, and may be designed for this purpose. In some cases, the chamber system may be inserted via a catheter and configured accordingly. Alternatively, a combination of open surgery and catheter-based procedures is also possible.

The fluid present in the chambers when the chamber system is in use, may be any fluid that displays the necessary flow properties.

The connection channel which connects the first chamber to the second chamber preferably has a diameter of 0.5 cm to 5 cm, particularly preferably a diameter of 15 mm to 20 mm. The connection channel which connects these chambers to each other preferably has a length of 1 mm-500 mm, particularly preferably a length of 1 mm-100 mm, most preferably a length of 2 mm-10 mm.

The chambers may already be filled with fluid before implantation of the chamber system. The fluid preferably consists of a fluid of low viscosity, preferably a mixture of liquids, particularly preferably comprising water ($H_2O$) and/or having an isotonic property. Further, the fluid may particularly preferably be or comprise air, more preferably it may consist of a defined gas mixture. The gas or gas mixture may particularly preferably be or comprise helium.

In several embodiments according to the invention, the chambers can be filled with fluid after implantation, i.e. when they are already located and arranged in the body. They can be prepared or designed accordingly, e.g. have an opening—preferably closable by a closure device. This arrangement in the body may be a preliminary or a final position of the chambers in the body. Filling or correcting the degree of filling or the fluid volume contained in the chambers after arrangement or implantation may advantageously enable adaptation of the chamber system to the needs of the specific patient, which in several embodiments may also take place at a point in time significantly after implantation.

In some embodiments according to the present invention, the displacement of the fluid from one chamber into the connected other chamber is operated or brought about solely by changing the heart volume within the heart sac.

In several embodiments according to the present invention, the chamber system encompasses a support device. The at least two chambers, the first and the second chamber, may together with the connection channel form exactly one closed bag, wherein the support device may form or give structure to the connection channel at least in sections. The support device may be a hollow body, e.g. a, e.g. flexible, deformable, support device, in particular a stent, a ring or a cylinder, that surrounds the connection channel to form or give structure to the connection channel at least in sections.

In several embodiments, the diameter of the connection channel between the chambers is kept constant by a device—which preferably expands after its implantation—which may be connected to the wall of the connection channel. Preferably, this device is a stent. Particularly preferably, the stent keeps the opening in the heart sac open to an optionally predetermined size. Particularly preferably, the stent is made of or comprises memory material (nitinol or polymer).

In several embodiments, the connection channel that connects the chambers consists of an elastic polymer or polymer film, which preferably adapts to the diameter of the channel.

In several embodiments, the chamber walls (also: the chamber wall) consist of or comprise an elastic polymer film which adapts to the variable volume of the fluid present in the chamber.

The chamber system is preferably designed for the at least partial or sectional implantation into the heart sac and the chest and/or the abdominal cavity. The device is preferably designed such that it may be at least partially implanted in a heart sac.

In several embodiments, the device is designed such that a section may be implanted in the heart sac and/or in the chest cavity and/or in a further section in the abdominal cavity.

In some embodiments of the chamber system according to the present invention, it is designed such that several chambers may be located in the heart sac, in the chest and/or in the abdominal cavity and/or outside the body at the same time.

Preferably, the first chamber is located in the heart sac and is in fluid communication with the second chamber via the connecting channel.

In several embodiments, the second chamber is the atmosphere or has fluid communication therewith. In several embodiments, the second chamber is intended to be located outside of the patient's body after implantation.

In some embodiments, the second chamber is intended to be located within the body after implantation.

In several embodiments, the second chamber is intended to be located within the abdominal cavity after implantation. In several embodiments, the second chamber is intended to be located in the right chest cavity after implantation.

In some embodiments, the second chamber is intended to be located in the left chest cavity after implantation.

In several embodiments, several second chambers are intended to be located inside and/or outside the body after implantation.

In some embodiments, the chamber system according to the present invention comprises a stent in or on the section of the channel that connects the chambers.

In several embodiments, such a stent may be the only section of the chamber system that comprises a metal or an alloy.

In some embodiments, the chamber system consists of the chambers and their connecting channels, optionally further comprising the support device and/or a support framework for supporting the shape of the chambers.

In several embodiments, the chambers collectively form a sealed fluid system. This, at least in use, preferably does not have an inlet or outlet and/or is preferably not fluidically connected to an exterior of the chamber and/or of the patient.

In some embodiments, the chambers have a predetermined shape, while in others they do not.

In several embodiments, the shape of at least one of the chambers is supported by a frame or rack.

In some embodiments, the shape of at least one of the chambers is supported by a frame having memory properties or shape memory properties.

In several embodiments, the shape of at least one of the chambers is supported by a stent.

In some embodiments, the chambers may support a flow direction of fluid within or between the chambers through an own elastic force.

In several embodiments, at least two chambers, e.g., the first chamber and the second chamber or further chambers, of the chamber system according to the invention, or their chamber walls, have different elasticities, elasticity moduli (E-Moduli, strain moduli, or Young's moduli), and/or internal volumes (e.g., in a state without liquid and/or without external action, or in a relaxed state) from each other.

The chamber system according to the present invention preferably supports the displacement of the heart apex towards the base of the heart. The device thereby supports the shortening of the long axis of the heart. The device thereby increases the volume of blood that may be ejected from the heart by shortening the long axis.

In several embodiments, the chamber system comprises, or is connected to, sensors. The sensors may be pressure sensors and/or position sensors. The sensors are thereby preferably provided and suitable to measure physiological parameters related to or associated with the filling of the chambers, the pressure in the chambers, the flow of the fluid, and/or the heart activity. In this, the sensors are preferably designed such that to provide a sensor signal that is transmitted to at least one device in the patient's body and/or outside the patient's body, e.g., wirelessly or wired. Corresponding emitters and/or receivers for the signal may be provided.

The device receiving such sensor signals may be a control unit of the chamber system connected to at least one device for controlling or regulating the flow or flow rate of the fluid between the chambers. Such devices for controlling or regulating the flow of the fluid between the chambers, wherein these devices may be part of the chamber system, may include valves, throttles and other adjustable flow or flow limiters such as orifices, etc.

The chamber system according to the present invention may thus have actuators which act for example on devices for controlling or regulating the flow of fluid between the chambers which devices may be provided for example in the connection channel or in the support device. However, these devices, for the actuation of which a drive unit may be provided in the chamber system, which may be supplied with energy, for example, from a battery or in some other way, preferably do not act on the heart muscle, which is why, in the sense of the present invention, they are not a motor for acting on the heart function, do not support the heart activity and/or do not support the heart chambers or do not actively support them.

In several embodiments, the chamber system according to the present invention comprises, or is connected to, sensors that measure the electrical heart activity, pressure sensors (that measure for example the blood pressure in vessels and/or in one or more heart chambers), sensors for force, electrical voltage and/or electrical current, pressure and/or for the extent of the change of shape of at least one of the chambers.

In several embodiments, the chamber system according to the present invention comprises a device and/or sensors for obtaining an ECG (electrocardiogram) signal.

In some embodiments, it is provided that the devices for controlling or regulating the flow of fluid between the chambers, are controlled synchronously with the heart activity. The chamber system may be programmed accordingly.

During the entire heart cycle, the heart apex remains almost stationary, which is caused, among other things, by the heart sac. The heart sac is a closed sac that contains around 10 ml of liquid and surrounds the entire heart. The closed heart sac is liquid-tight and thus does, therefore, not allow liquid exchange with the surrounding body cavities. When the heart contracts, the heart sac, which is partially exposed freely in the chest, can follow the reduction in the circumference of the heart. However, the heart sac is connected in the region of the heart apex to the sternum and the processus xiphoideus by the sterno-pericardial ligament and lies firmly connected to the diaphragm. During contraction of the heart, the heart sac and the heart apex lying in the closed heart sac cannot move from the chest wall towards the heart base. For this reason, the contraction of the heart muscle and the shortening of the heart lead to a pull on the base of the heart and the elastic aortic root, which is thus stretched in the systole. As soon as the heart muscle relaxes in the diastole, the stretched aortic root pulls the heart base away from the stationary heart apex due to the tension energy stored in it. Studies with sheep, which have anatomy comparable to humans with respect to the heart, show that, at rest due to tension, there is a force between the aortic root and the heart base of 1.8±0.2 N. To move the aortic root 10 mm towards the heart apex, a force F of 1.8±0.1 N must be applied. The normal deflection of the displacement(s) of the aortic root is 12±2 mm in healthy people. Thus, per heartbeat, to deflect the aortic root, work W of approximately $W=F*s=1.8$ N*0.012 m=0.0216 J is required, wherein the corresponding energy is partly stored in the elastic stretch of the aortic root.

Heart weakness, in particular heart failure, occurs when the heart can only eject less than 45% of the ventricular volume. An ejection rate of less than 35% is considered a severe impairment.

Symptoms of heart failure include shortness of breath (exertional dyspnea, resting dyspnea, orthopnea, paroxysmal nocturnal dyspnea), fatigue, inadequate exhaustion after exertion, weakness, lethargy, liquid retention (leg or abdominal swelling, weight gain), nocturnal urination (nocturia), dry cough (especially at night), dizziness, syncopes, loss of appetite, nausea, bloating, meteorism, constipation, abdominal pain, possibly weight loss, memory disorders, states of confusion and cognitive impairments.

Heart failure is classified according to severity into NYHA I (diagnosed heart disease without symptoms and without limitation of exercise capacity), NYHA II (mild limitation of exercise capacity, no symptoms at rest, but only with greater exercise), NYHA III (severe limitation of exercise capacity, no symptoms at rest, but already with mild exercise) and NYHA IV (persistent symptoms even at rest). When diagnosing heart failure, echocardiography is particularly important, with which regional and global limitations of the heart function can be assessed.

Patients with heart failure with a left ventricular ejection fraction (EF) of less than 45% show a decreased displacement of the aortic root to less than 8 mm during the systole. The shortening of the long axis of the heart is a particularly sensitive parameter for measuring heart function.

In a heart failure with reduced ejection fraction (HFrEF), there is measured in echocardiography reduced wall motion of the heart with reduced ejection fraction of less than 45%. It can be seen that the shortening of both the long axis from the heart apex to the heart base and the short axis orthogonal to it is reduced. With two-dimensional echocardiography (Simpson method), the reduction in ejection volume can be determined.

At least half of the patients with symptoms of heart failure have normal cardiac function as measured by conventional echocardiography with a normal shortening of the orthogonal diameter of the ventricles. The ejection fraction calculated from this appears normal. This form of heart failure is referred to as heart failure with preserved ejection fraction (HFpEF). Stiffening of the heart muscles and impaired diastolic function of the heart are discussed as causes for heart failure. However, a closer echocardiographic examination of the cardiac function of these patients often reveals a change in the twisting and untwisting of the left ventricle as well as a reduction in the diastolic suction and the early diastolic filling of the left ventricle.

The normal movement of the aortic root with the heart base towards the heart apex of 12±2 mm is reduced to significantly less than 8 mm. The speed of the stroke of the aortic root in the systole and the early diastole is highly significantly reduced with 0.64±0.51 cm/s compared to 1.54±0.51 cm/s in the systole and 1.49±0.77 cm/s compared to 2.32±1.24 cm/s at the start of the diastole. The poor performance and the symptoms of heart failure in these patients correlate with a lower level of elasticity, in particular a stiffening of the aortic root. At the same time, thickening of the heart muscle is found in these patients, suggesting compensation for the lower windkessel function and a smaller stroke of the aortic root. The heart force still appears normal or even increased in echocardiography, but is no longer sufficient to pull the aortic root towards the heart apex, since this is less elastic and an increased force would be required to bring about a sufficient stroke of the aortic root. The reduced shortening of the long axis of the heart results in a reduction in stroke volume The chamber system according to the present invention should preferably be used in chronic heart failure with preserved left ventricular ejection fraction (HFpEF), in which the systolic heart muscle function is largely preserved, but the cardiac strength is no longer sufficient to stretch an aortic root stiffened by various diseases or aging processes and, associated therewith to produce a sufficient stroke of the heart base or stretching of the aortic root.

In several embodiments according to the present invention, the chambers of the medical chamber system comprise at least two separate bags, which are connected directly or indirectly to form a common fluid space. The connection of the two separate bags may be a sleeve, which may be referred to as a connecting channel between the two bags. The two bags may be pushed or slipped onto the sleeve, in particular onto the two sleeve ends, by adapter-shaped connection openings. In addition, the bag openings may be fixed to the sleeve, for example by a seam, a gluing or the like.

In several embodiments according to the present invention, the total volume of the chambers is between 0.1 ml and 100 ml, in particular between 1 ml and 50 ml.

In several embodiments according to the present invention, the medical chamber system is completely or partially sterile.

Several of the embodiments according to the present invention may have the following advantages:

The chamber system according to the present invention advantageously allows the displacement of the heart apex towards the heart base to support the heart activity.

Unlike the normal shortening of the long heart axis during the systole by displacing the heart base towards the heart apex, the chamber system according to the present invention advantageously enables the heart apex to be displaced towards the heart base.

By restoring the shortening of the long heart axis during the systole, the ejection of the amount of blood from the heart may advantageously be increased by the chamber system according to the present invention.

Restoring the shortening of the long heart axis by the chamber system according to the present invention advantageously leads to better emptying of the heart chambers and reduces the end-systolic volume in the heart. The heart chamber may therefore take up more volume in the diastole and eject more blood in the systole, which increases the effectiveness of the heart function and lowers the pressure in the left atrium.

In patients with HFpEF, the stretching and stroke of the stiffened aortic root are reduced. In these patients, heart strength is normal or compensatory enlarged. The lack of shortening of the heart chambers during the systole cannot be compensated for by an additional reduction in the diameter of the ventricle and causes a reduction in the ejection volume. The chamber system according to the present invention advantageously supports the displacement of the heart apex, thus replacing the displacement of the heart base, which is no longer possible, with a displacement of the heart apex. This leads to a shortening of the longitudinal axis of the heart and thus to an improved ejection capacity or performance of the heart.

A positive, advantageous effect of the chamber system according to the present invention on muscle contraction of the two ventricles and the two atria may be a side effect.

In the following, the device according to the present invention is described on the basis of preferred embodiments thereof with reference to the attached figures. However, the present invention is not limited to these embodiments. The following applies in the figures:

FIGS. 1A and 1B show a representation of a heart with the four heart chambers, heart base and heart skeleton;

FIG. 3 shows a representation of the suspension of the heart sac in the chest;

FIGS. 5A and 5B show a schematic representation of the normal pumping function of the left ventricle;

FIG. 8A to 8D show an insertion catheter for placement of the chamber system according to the present invention;

Figures 10A, 10B:
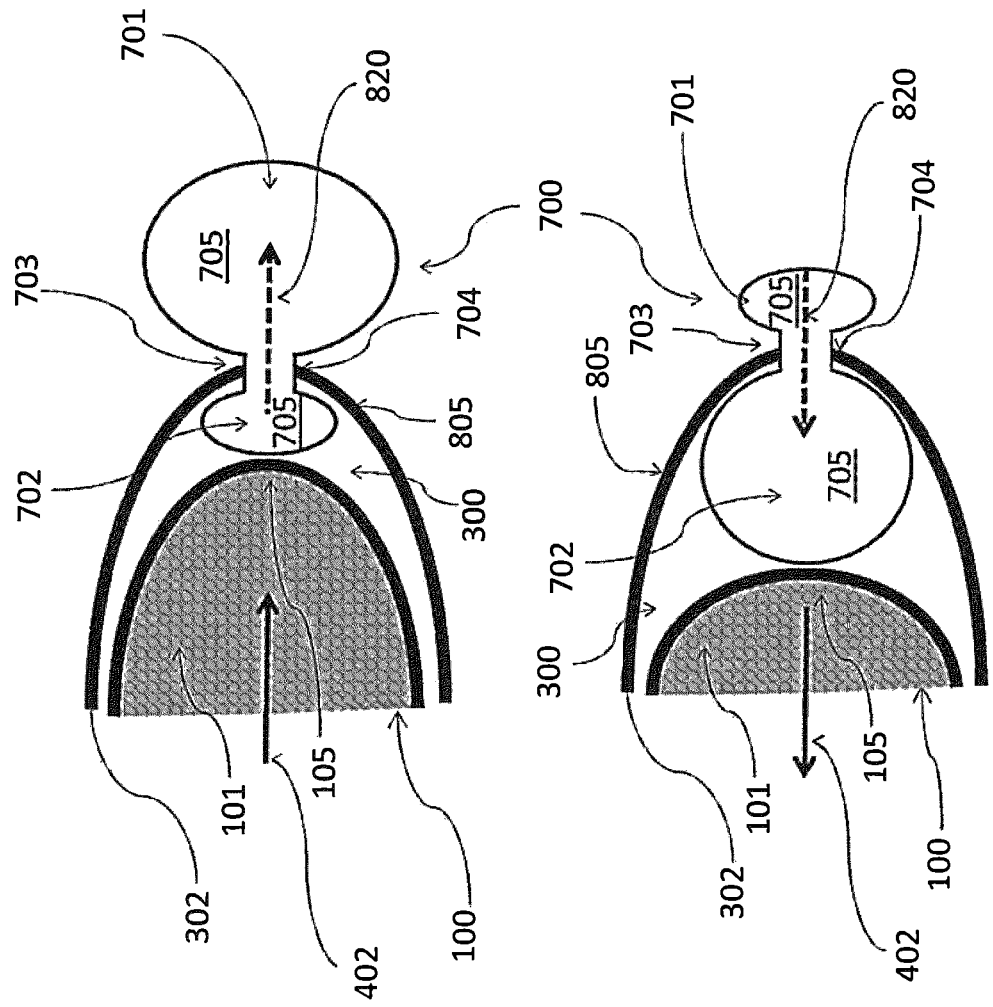
Figures 11A, 11B:
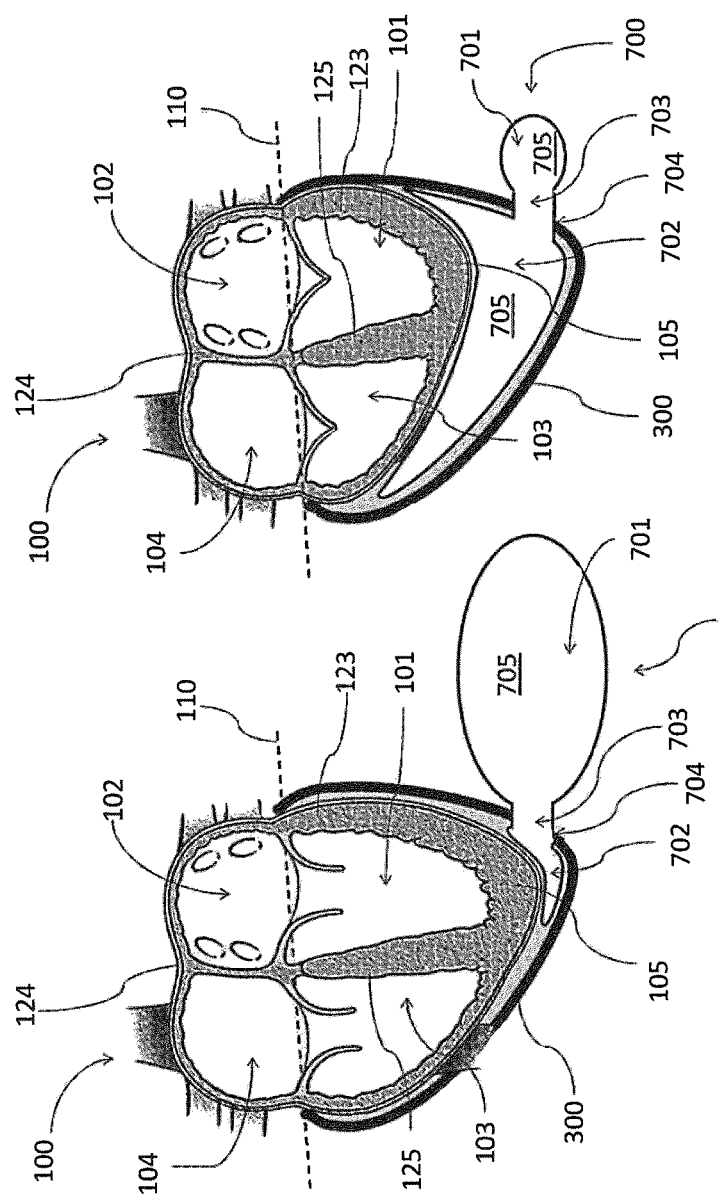

FIGS. 10A and 10B schematically show the function of the chamber system according to the present invention; and FIGS. 11A and 11B show the chamber system according to the present invention in the heart sac with heart.

FIGS. 1A and 1B show a human heart 100 with the four heart chambers and the heart base.

FIG. 1A shows the left ventricle 101 (left lower heart chamber) and the left atrium 102 (left upper heart chamber) with the mitral valve 111 disposed in between, the right ventricle 103 (right lower heart chamber) and the right atrium 104 (right upper heart chamber) with the tricuspid valve 112 disposed in between. The interatrial septum 124 is disposed between the two atria and the interventricular septum 125 is disposed between the two ventricles 101 and 103.

In FIG. 1B, the heart base 110 is shown. The heart base is a, more or less flat, anatomical structure of the heart, in or on which the two atrioventricular valves, namely mitral valve 111 and tricuspid valve 112, and the two semilunar valves, namely the aortic valve 113 and the pulmonary valve 114, are disposed. The heart skeleton 120 consists of cartilaginous tissue and is the only rigid structure of the heart. The heart skeleton 120 completely encompasses the aortic root 201 and the central parts of the mitral valve ring 131 and the tricuspid valve ring 132. The most vigorously formed portions of the heart skeleton 120 are the left fibrous trigone 121 and the right fibrous trigone 122. On the right fibrous trigone 122, the mitral valve 111 and the tricuspid valve 112 adjoin each other. The heart muscle 123 of the interventricular septum 125 is connected to the heart skeleton 120 in the area of the right fibrous trigon 122 between the mitral valve 111 and the tricuspid valve 112. At this point, the contraction of the heart muscle 123 and above all of the interventricular septum 125 leads to a pull or traction on the heart skeleton 120 and the therewith connected aortic valve 113 towards the heart apex.

The mitral valve 111 and tricuspid valve 112 close at the end of the diastole and ensure that when the ventricles 101 and 103 contract, the blood does not flow back into the atria 102 and 104 but is pumped forward and, on the right side, into the lungs and, on the left side, into the body's circuit. The aortic valve 113 and the pulmonary valve 114 close at the end of systole and ensure that, after the contraction of the two ventricles 101 and 103, the blood does not flow back into the ventricles 101 and 103, but rather that the diastolic blood pressure is maintained in the pulmonary artery and lungs on the right side and that the diastolic pressure is maintained in the aorta and the body's circuit on the left side.

Figure 2A:
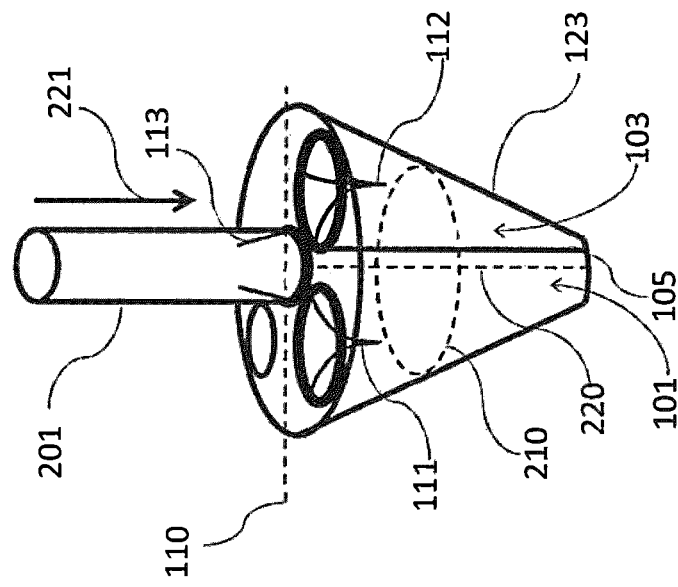
FIGS. 2A and 2B show a representation of the pumping function of the heart.
Figure 2B:
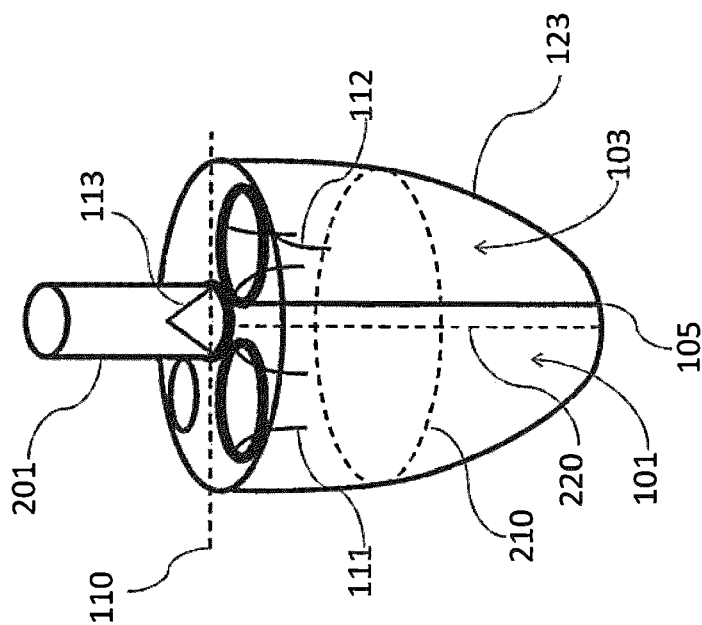

FIGS. 2A and 2B show a schematic representation of the heart.

FIG. 2A shows the heart in the diastole with relaxed heart muscle 123. The longitudinal axis 220 is longest here in the contraction cycle and the circumference 210 of the ventricles 101, 103 and the orthogonal diameter are largest. The two ventricles 101 and 103 are filled; the mitral valve 111 and tricuspid valve 112 are open to enable blood inflow into the ventricles. The aortic valve 113 is closed and thus prevents the backflow of blood from the body's circuit into the left ventricle and maintains the diastolic blood pressure in the body. The aortic root 201 is maximally contracted at the end of the diastole.

FIG. 2B schematically shows the contraction of the heart in the systole with a normally elastic aortic root 201. The heart muscle 123 is contracted, the heart has the smallest circumference 210 and the smallest orthogonal diameter in the heart cycle. The heart apex 105 remains stationary, the heart base 110 has shifted to the heart apex (movement direction of the heart base 221), and the longitudinal axis 220 is the shortest. The atrioventricular valves 111 and 112 are closed in order to prevent a back flow of blood into the two atria 102 and 104. The aortic valve 113 is open to enable ejection of blood into the body's circuit. The aortic root 201 is maximally stretched.

FIG. 3 shows a schematic representation of the chest of a human being. The heart sac 300 rests on the diaphragm 302 and is stretched between the aortic root 201 with the mediastinum 306 and the sterno-pericardial ligament 301. The sterno-pericardial ligament 301 extends from the heart sac 300 in the area of the heart apex 105 to the end of the sternum 303 in the area of the xiphoid process 304 and the rib 305.

As the heart contracts, the heart sac 300 may follow the reduction in heart circumference 210 during the systole. Since however the closed heart sac is stretched between the relatively immobile sternum 303 and the mediastinum 306 via the sterno-pericardial ligament 301, the heart apex 105 cannot move away from the sternum 303 in the direction of the heart base 110. For this reason, contraction of the heart and shortening of the longitudinal axis 220 of the heart results in traction on the heart base 110 and the elastic aortic root 201, which is thus stretched in the systole and the heart base 101 with the aortic root 201 is pulled toward the heart apex 105.

Figure 4C:
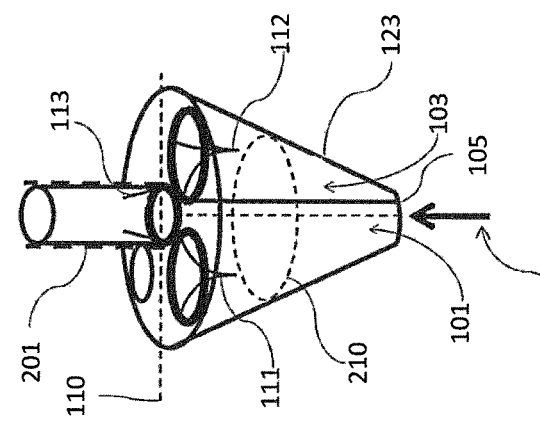
FIG. 4A to 4C show a representation of the pumping function of the heart with stationary heart base.
Figure 4B:
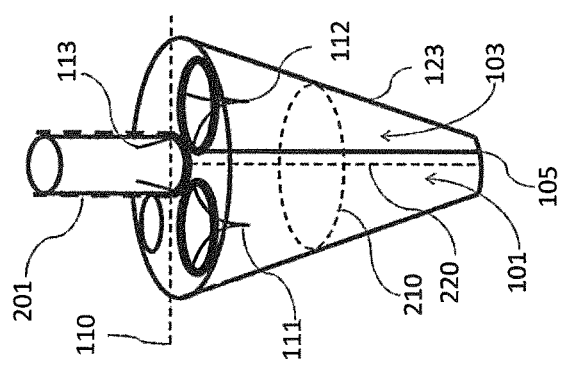
Figure 4A:
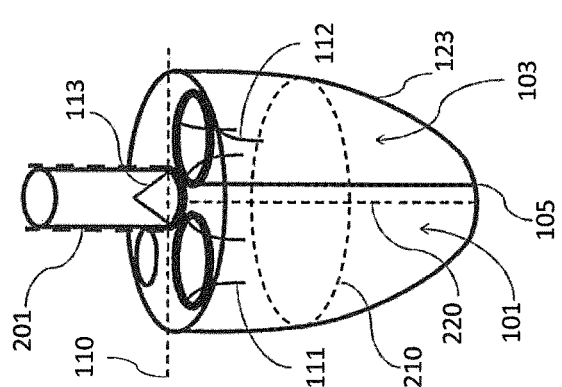

FIG. 4A to 4C schematically show the contraction of the heart in the systole as well, but with a stiff, non-elastic aortic root 201 and a stationary heat base 110.

FIG. 4A shows the heart in the diastole with relaxed heart muscle 123. The longitudinal axis 220 is longest here in the contraction cycle and the circumference 210 of the ventricles 101, 103 and the orthogonal diameter are largest. The two ventricles 101 and 103 are filled; the mitral valve 111 and tricuspid valve 112 are open to allow blood inflow into the ventricles. The aortic valve 113 is closed and thus prevents the backflow of blood from the body's circuit into the left ventricle and maintains the diastolic blood pressure in the body.

FIG. 4B shows the heart with contracted heart muscle 123, the heart has the smallest circumference 210 and the smallest orthogonal diameter in the heart cycle. The heart apex 105 remains stationary, the position of the heart base 110 has not changed in relation to the diastole, since the stiff aortic root 201 cannot be stretched and so the heart base 110 cannot be drawn towards the heart apex 105. The longitudinal axis 220 is as long as in the relaxed heart in the diastole in FIG. 4A. However, due to muscle contraction, the circumference 210 and the orthogonal diameter are the smallest in the heart cycle. The atrioventricular valves 111 and 112 are closed to prevent a backflow of blood into the two atria 102 and 104. The aortic valve 113 is open to enable ejection of blood into the body's circuit.

FIG. 4C shows the heart with a contracted heart muscle 123 while using the chamber system according to the present invention. The heart base 110 remains stationary as in FIG. 4B. the longitudinal axis 220 is shortest as in FIG. 2B, since the chamber system according to the present invention enables that the heart apex 105 may move towards the heart base 110 (movement direction 402 of the heart apex). The atrioventricular valves 111 and 112 are closed to prevent a backflow of blood into the two atria 102 and 104. The aortic valve 113 is open to enable ejection of blood into the body's circuit The heart muscle 123 is relaxed, the longitudinal axis 220 is longest and the circumference 210 of the ventricles 101 and the orthogonal diameter are largest in the heart cycle. The ventricle 101 is filled and the mitral valve 111 is open to enable the blood flow 401 into the ventricle. The aortic valve 113 is closed and thus prevents the backflow of blood from the body's circuit into the left ventricle 101 and maintains the diastolic blood pressure in the body. The aortic root 201 is maximally contracted at the end of the diastole.

FIG. 5A shows schematically a left ventricle 101 in the diastole. The heart muscle 123 is relaxed, the longitudinal axis 220 is longest and the circumference 210 of the ventricles 101 and the orthogonal diameter are largest in the heart cycle. The ventricle 101 is filled and the mitral valve 111 is open to enable the blood flow 401 into the ventricle. The aortic valve 113 is closed and thus prevents the backflow of blood from the body's circuit into the left ventricle 101 and maintains the diastolic blood pressure in the body. The aortic root 201 is maximally contracted at the end of the diastole.

Figure 6A:
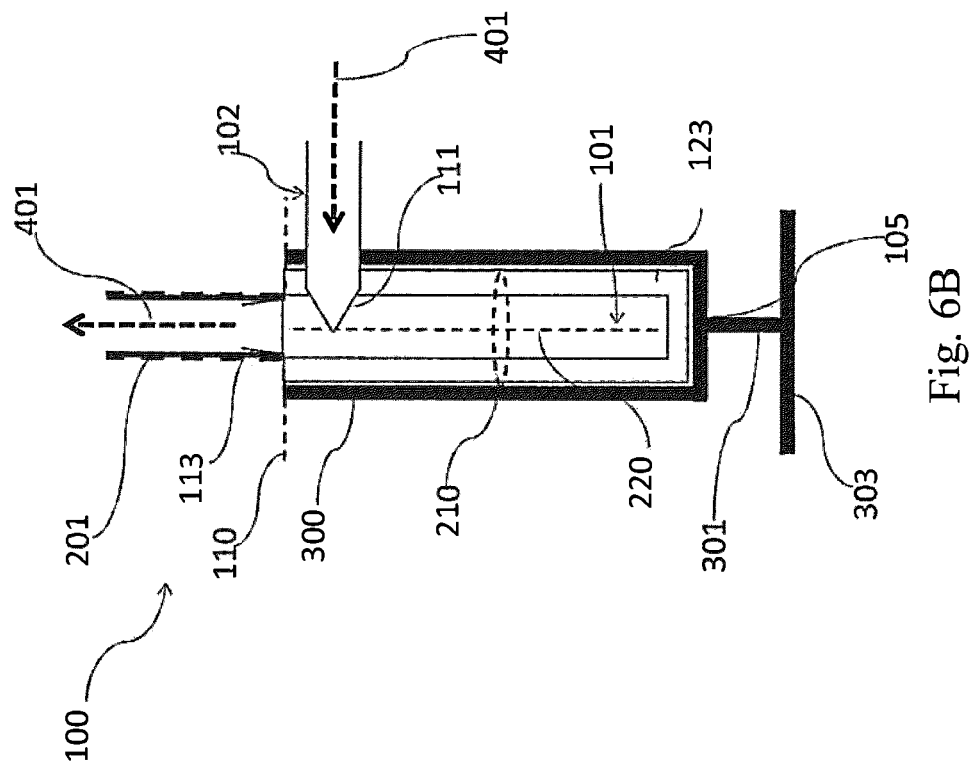
FIGS. 6A and 6B show a schematic representation of the pumping function of the left ventricle with stationary heart base.

FIG. 6A shows schematically a left ventricle 101 in the diastole, however with a stiff, non-elastic aortic root 201. The situation is substantially identical to the one in FIG. 5A. The heart muscle 123 is relaxed, the longitudinal axis 220 is longest and the circumference 210 of the ventricle 101 and the orthogonal diameter are largest in the heart cycle. The ventricle 101 is filled and the mitral valve 111 is open to enable the blood flow 401 into the ventricle. The aortic valve 113 is closed and thus prevents the backflow of blood from the body's circuit into the left ventricle 101 and maintains the diastolic blood pressure in the body. The aortic root 201 is maximally contracted at the end of the diastole.

Figure 6B:
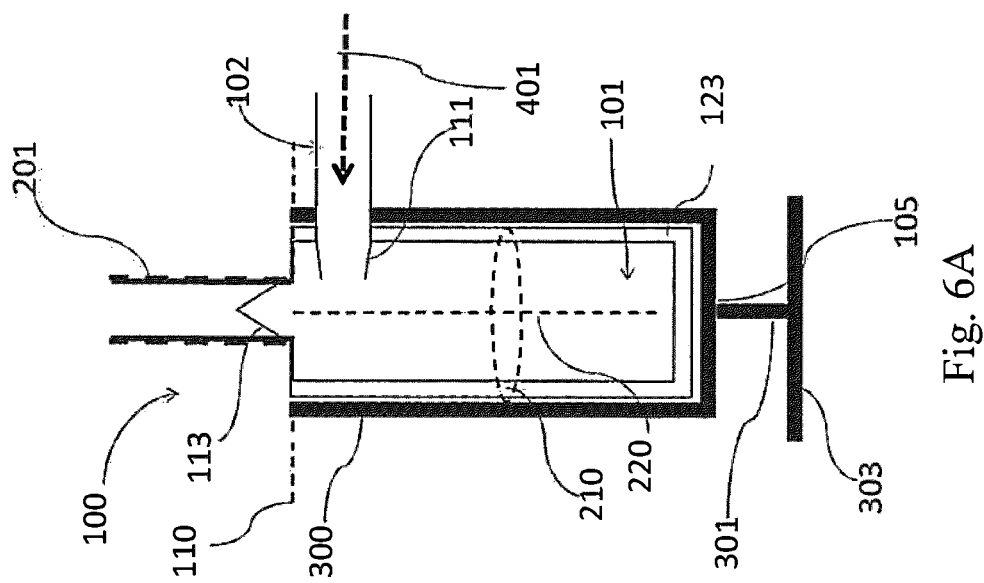

FIG. 6B schematically shows contraction of the left ventricle 101 with a stiff, nonelastic aortic root 201. The heart muscle 123 is contracted. The heart apex 105 remains stationary since the heart sac 300 is connected to the sternum 303 via the sterno-pericardial ligament 301. The position of the heart base 110 has not changed since the stiff aortic root 201 cannot be stretched and thus the heart base 110 cannot be drawn towards heart apex 105. The longitudinal axis 220 is as long as that in the relaxed heart in the diastole in FIG. 4A. However, because of the muscle contraction, the circumference 210 and the orthogonal diameter are smallest, which applies in the entire heart cycle. The mitral valve 111 is closed in order to prevent backflow of blood into the left atrium 102. The aortic valve 113 is open to allow ejection of blood into the body's circuit.

Figures 7A, 7B:
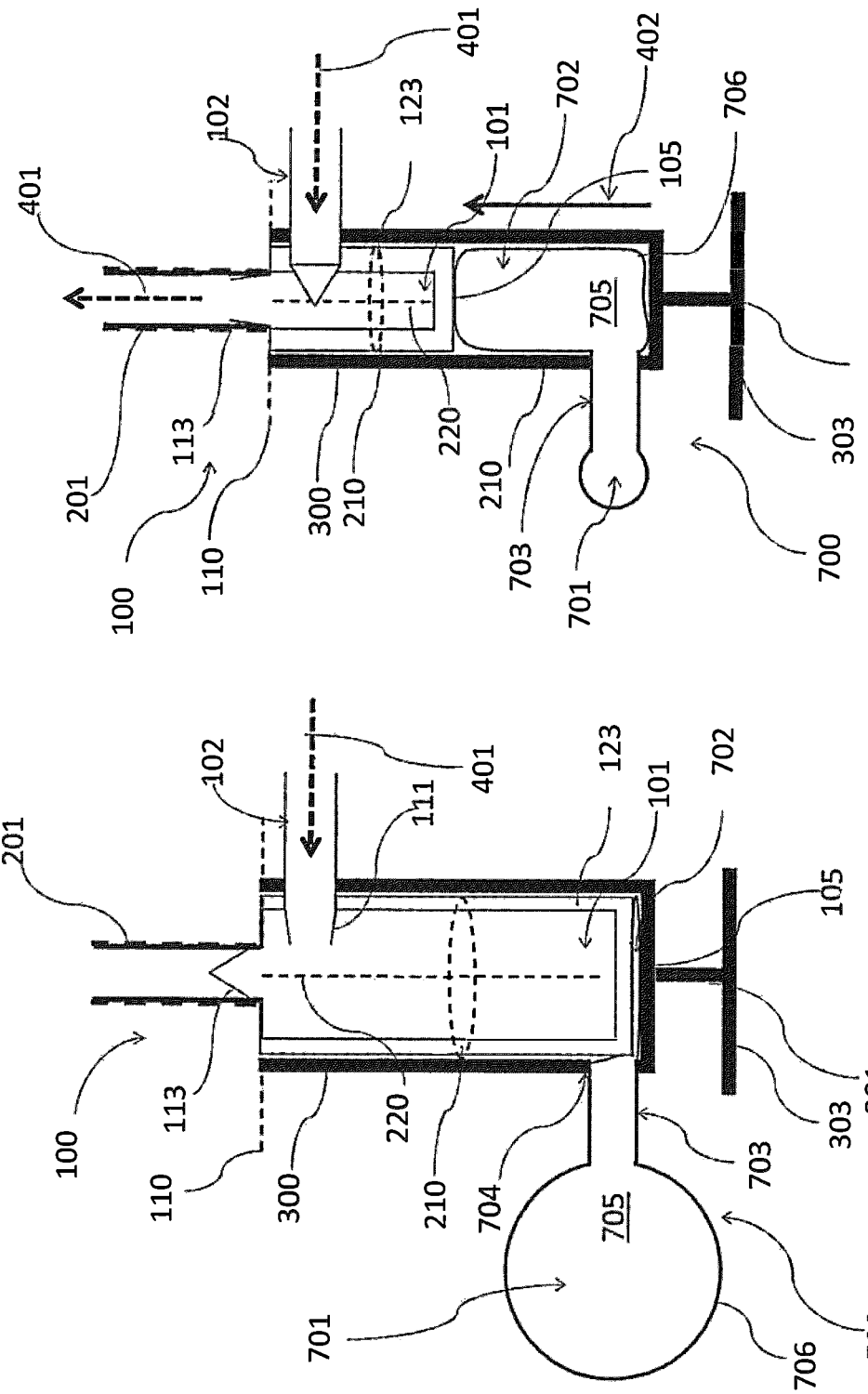
FIGS. 7A and 7B show a schematic embodiment of the chamber system according to the present invention, which enables a displacement of the heart apex with a stationary heart base.

FIGS. 7A and 7B show the function of an embodiment of the chamber system 700 according to the present invention with reference to a schematically outlined heart sac 300 of a schematically outlined heart 100.

FIG. 7A shows a schematic representation of the heart 100 in diastole. The chamber system 700 according to the present invention comprises or consists of a second chamber 701 outside the heart sac 300, a first chamber 702 inside the heart sac 300, and the connection channel 703 between the chambers 701 and 702, wherein the connection channel 703 passes through an opening 704 in the heart sac 300.

The first chamber 702 is shrunk and thus allows a maximum expansion of the heart 100 and a maximum filling of the heart chamber 101 in the diastole. Almost all of the fluid provided in the chamber system 700 is present in the second chamber 701.

FIG. 7B shows an embodiment of the chamber system 700 according to the present invention in the heart sac 300 with heart 100. In this, FIG. 7B shows a schematic representation of the heart 100 in the systole and the chamber system 700 according to the present invention with the second chamber 701 outside the heart sac 300, the first chamber 702 in the heart sac 300 and the connection channel 703 between the chambers 701 and 702. The connection channel 703 passes through a hole or an opening in the heart sac 704. The first chamber 702 is expanded to allow displacement of the heart apex 105 in the movement direction 402 toward the heart base 110, thus allowing maximum shortening of the long axis 220 of the heart chamber 101 and thus maximum emptying of the heart chamber 101. The fluid of the chamber system 700 is almost entirely present in the first chamber 702, and the second chamber 701 has shrunk or became smaller.

FIGS. 8A to 8D show the insertion of the chamber system 700 according to the present invention.

FIG. 8A shows the chamber system 700 according to the present invention fully received in an insertion catheter 800.

The tip 801 of the insertion catheter 800 has overcome the heart sac wall 805 by the opening 704 and is present within the heart sac.

FIG. 8B shows the chamber system 700 advanced in the direction of the tip 801 of the insertion catheter 800, so that the first chamber 702 has left the insertion catheter 800 through its end-side lumen and has expanded in the heart sac 300.

The connection channel 703, which may also be designed to be elastic or expandable, is still present in the lumen of the insertion catheter 800 in the phase of implantation shown in FIG. 8b and is prevented from radial unfolding by inner walls of the insertion catheter 800.

FIG. 8C shows the tip 801 of the insertion catheter 800 further retracted. The connection channel 703 and the stent 810 lie outside the lumen of the insertion catheter 800 and have unfolded, such as by a shape memory of the stent 810, and have radially enlarged the opening 704 in the heart sac 300. The stent 810 is anchored to or adheres to the heart sac wall 805, such as by radial force.

FIG. 8D shows the insertion catheter 800 further retracted so that the second chamber 701 has also expanded, and namely outside the heart sac 300.

In relation to this embodiment, the chamber system 700 is thus completely outside of the insertion catheter 800. The latter is no longer needed and can be discarded.

A tool which is not shown here, e.g., a so-called pusher, may be used to remove the chamber system 700 out of the insertion catheter 800.

Figure 9:
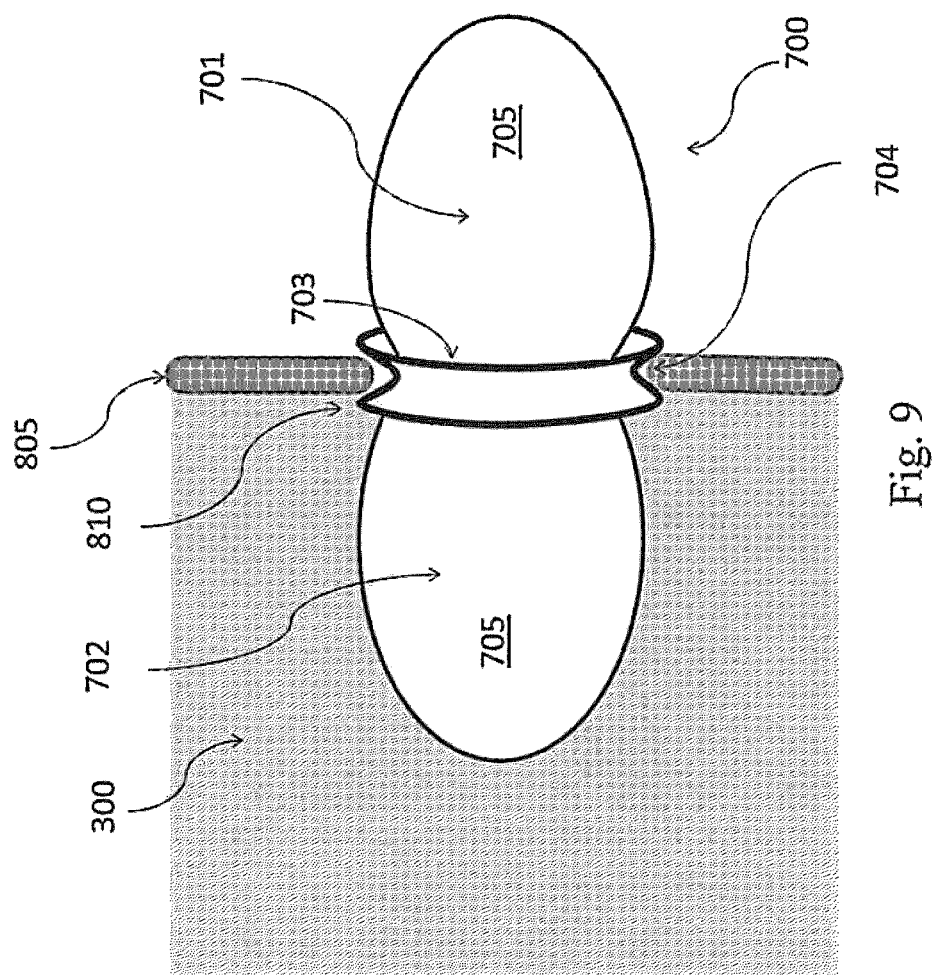
FIG. 9 shows the chamber system according to the present invention in the heart sac.

FIG. 9 shows a perspective, three-dimensional view of the stent 810 unfolded and anchored in the opening of the heart sac wall 805. Both chambers 701 and 702 are expanded.

The chambers 701 and 702 have a volume of 0 ml-500 ml, particularly preferably a volume of 0.01 ml-300 ml, more preferably a volume of 0.10 ml-200 ml, very particularly preferably a volume of 1.00 ml-100 ml.

The proportion of the fluid that is moved between the chambers 701 and 702 has a proportion of the total volume of the fluid of 0.1%-20%, particularly preferably a proportion of the total volume of the fluid of 1%-50%, particularly preferably a proportion of the total volume of the fluid from 10%-90%.

The connection channel 703, which connects the chambers 701, 702 to each other, preferably has a diameter of 0.5 cm-5 cm. Particularly preferably a diameter of 15 mm-20 mm.

The connection channel 703, which connects the chambers 701, 702 to each other, preferably has a length of 1 mm-500 mm. Particularly preferably a length of 1 mm-100 mm. Particularly preferably a length of 2 mm-10 mm.

The fluid in the chambers 701, 702 may be any fluid having the necessary flow characteristics. Preferably, the connection channel 703 that connects the first chamber 702 in the heart sac 300 to the second chamber 701 outside the heart sac 300 has a sufficiently large diameter and the fluid has a sufficiently low viscosity so that only minimal energy losses occur when the fluid is moved between the two chambers.

The size ratios of chambers 701, 702 shown in the preceding figures are purely for illustrative purposes. The ratios shown between the chamber volumes are of no significance.

FIGS. 10A and 10B schematically show the function of an embodiment of the chamber system 700 according to the present invention with heart sac 300 and with heart 100.

FIG. 10A schematically shows a representation of the heart 100 at the end of the diastole and the chamber system 700 according to the present invention with a chamber 701 outside the heart sac 300, a chamber 702 inside the heart sac 300 and the connection channel 703 between the chamber 701 and 702. Wherein the connection channel passes through an opening 704 in the heart sac wall 805. As a result of the filling of the heart chamber 101 in the diastole, the heart apex 105, represented by the arrow 402, acts on the first chamber 702, which is thereby reduced in size, allowing maximum extension of the longitudinal axis of the heart chamber 101 and maximum filling of the heart chamber 101. The fluid 705 thereby moves, represented by arrow 820, from the first chamber 702 into the second chamber 701.

FIG. 10B schematically shows a representation of the heart 100 at the end of the systole and the chamber system 700 according to the present invention, which is present with the second chamber 701 outside the heart sac 300 and with the first chamber 702 inside the heart sac 300, wherein the connection channel 703 lies between the chambers 701 and 702, wherein the connection channel 703 passes through the opening 704 in the heart sac wall 805.

As a result of the contraction of the ventricle 101 in the systole, the heart apex 105, represented by the arrow 402, moves away from the chamber 702, which thereby enlarges and thus allows a maximum shortening of the longitudinal axis of the ventricle 101 and maximum emptying of the ventricle 101. The fluid 705 thereby moves, represented by arrow 820, from the second chamber 701 into the first chamber 702.

FIGS. 11A and 11B show the function of an embodiment of the chamber system 700 according to the present invention implanted within the heart sac 300 or the heart 100, respectively. The heart base 110 remains stationary throughout the entire heart cycle. By implanting the chamber system 700 according to the present invention with its first chamber 702 within the heart sac 300, the heart apex is mobile and can move toward the heart base 110 in the systole and away from the heart base 110 in the diastole.

FIG. 11A shows a representation of the heart 100 at the end of the diastole. The long axis of the heart is the longest here; the heart chambers 101 and 103 fill the heart sac 300 almost completely. The chamber system 700 according to the present invention is located with its second chamber 701 outside the heart sac 300, its first chamber 702 in the heart sac 300. The connection channel 703 passes through the opening 704 of the heart sac 300. Due to filling the heart chambers 101 and 103 in the diastole, the first chamber 702 has shrunk and thus allows maximum filling of the heart chambers 101 and 103. The fluid 705 is predominantly present in the second chamber 701. The first chamber 702 has adapted to the anatomical conditions within the heart sac 300 and the anatomical shape of the heart apex 105. The second chamber 701, which in this embodiment is located in the left chest cavity, has adapted to the anatomical conditions of the diaphragm (not shown) and of the lungs (not shown).

FIG. 11B shows a representation of the heart 100 toward the end of the systole. The heart muscle 123 with the interventricular septum 125 is contracted, the long axis of the heart is the shortest here. The heart apex 105 has shifted toward the heart base 110. The heart chambers 101 and 103 have emptied maximally. The chamber system 700 according to the present invention is unchanged with the second chamber 701 outside the heart 300 and the first chamber 702 inside the heart sac 300. By the contraction of the heart chambers 101 and 103 in the systole, the first chamber 702 is expanded and thus allows the heart apex 105 to be displaced towards the heart base 110 and, hence, a maximum emptying of the heart chambers 101 and 103. The fluid 705 is present predominantly in the first chamber 702. The first chamber 702 has adapted to the anatomical conditions in the heart sac 300 and the anatomical shape of the heart apex 105. The second chamber 701, which in this embodiment is located in the left chest cavity, has adapted to the anatomical conditions of the diaphragm (not shown) and of the lungs (not shown).

In several embodiments, the chamber system 700 according to the present invention may be implanted entirely surgically via an open-heart surgery or a lateral opening of the chest or via an opening of the abdominal cavity. Alternatively, in several embodiments, the chamber system 700 according to the present invention may be implanted via a combination procedure using a catheter and a surgical operation. Alternatively, in several embodiments, the chamber system 700 according to the present invention may also be introduced completely by a catheter and minimally invasive intervention in the area of the heart, in the area of both chest cavities or in the area of the abdominal cavity.

The chamber system 700 according to the present invention is introduced by a catheter preferably using the insertion catheter 800. The tip 801 of the insertion catheter 800 is inserted into the heart cavity, the chest or the abdominal cavity, as required. By a commonly used catheter and trocar, an opening 704 is created in the heart sac and enlarged by dilators and a dilatation balloon. The tip 801 of the insertion catheter 800 is advanced into the heart sac 300, allowing the first chamber 702 to exit the insertion catheter 800 and expand within the heart sac 300. Thereupon, the tip 801 of the insertion catheter 800 is retracted so that the connection channel 703 with the stent 810 unfolds in the opening 704 of the heart sac 300, thus enlarging and stabilizing it. The stent 810 is then anchored in the heart sac wall 805. The insertion catheter 800 is further retracted so that the second chamber 701 can also expand.

LIST OF REFERENCE NUMERALS 100 heart
101 left ventricle, left lower heart chamber
102 left atrium, left upper heart chamber
103 right ventricle, right lower heart chamber
104 right atrium, right upper heart chamber
105 heart apex
110 heart base
111 mitral valve
112 tricuspid valve
113 aortic valve
114 pulmonary valve
120 heart skeleton
121 left fibrous trigone
122 right fibrous trigone
123 heart muscle
124 atrial septum, atrium septum
125 interventricular septum, ventricle septum
131 mitral valve ring
132 tricuspid valve ring
201 aortic root
210 circumference of the ventricles in the diastole, orthogonal diameter
220 longitudinal axis of the ventricles
221 movement direction of the heart base
300 pericardium, heart sac
301 sterno-pericardial ligament
302 diaphragm, midriff
303 sternum
304 xiphoid process
305 rib
306 mediastinum, mediastinal area
401 blood flow or influx
402 movement direction of the heart apex
700 medical chamber system
701 second chamber outside the heart sac
702 first chamber in the heart sac
703 connection channel between the chambers
704 opening; hole in the heart sac
705 fluid
706 chamber wall
800 insertion catheter
801 tip of the insertion catheter
805 wall of heart sac
810 support device; stent
820 flow direction of the fluid

The invention claimed is:

1. A medical chamber system for implantation in a chest of a patient to support heart activity, the medical chamber system comprising at least a first chamber for arrangement inside a heart sac and a second chamber for arrangement outside the heart sac, wherein the chambers comprise a connection channel which connects the two chambers to each other, wherein the chambers and the connection channel are further embodied to be filled with fluid, wherein the first chamber and the second chamber together with the connection channel form exactly one closed bag in one-piece, wherein the connection channel forms a connection portion of the closed bag that connects the two chambers to each other, and wherein the medical chamber system further comprises a support device comprising a hollow body that surrounds the connection channel to form or give structure to the connection channel at least in sections.

2. The medical chamber system according to claim 1, wherein a chamber wall of the medical chamber system is flexibly deformable at least in sections.

3. The medical chamber system according to claim 1, wherein the support device is a flexibly deformable support device.

4. The medical chamber system according to claim 3, wherein the flexibly deformable support device is a stent, or a ring or a cylinder.

5. The medical chamber system according to claim 1, wherein a total filling volume of the chambers is, when added up, between 0.1 ml and 100 ml.

6. The medical chamber system according to claim 5, wherein the total filling volume of the chambers is, when added up, between 1 ml and 50 ml.

7. The medical chamber system according to claim 1, wherein the medical chamber system comprises sensors.

8. The medical chamber system according to claim 7, wherein the sensors comprise pressure sensors and/or position sensors.

9. The medical chamber system according to claim 1, wherein the medical chamber system, when implanted in the chest of the patient with the first chamber inside the heart sac and the second chamber outside the heart sac, supports the heart activity by displacing a heart apex.

10. The medical chamber system according to claim 1, wherein, when the medical chamber system is implanted in the chest of the patient with the first chamber inside the heart sac and the second chamber outside the heart sac, the chambers and the connection channel are arranged such that the heart activity acts on the first chamber and that the second chamber acts as a volume storage and/or an energy storage for the fluid.

11. A kit encompassing a medical chamber system according to claim 1 and an introduction system, wherein the introduction system comprises an insertion catheter, a guide catheter, a guide wire and/or at least one delivery or supply catheter.

* * * * *